United States Patent
Gross et al.

[11] Patent Number: 6,157,858
[45] Date of Patent: Dec. 5, 2000

[54] DEVICE FOR THE DELIVERY OF A SUBSTANCE TO A SUBJECT AND IMPROVED ELECTRODE ASSEMBLY

[75] Inventors: Joseph Gross, Dublin, Ireland; Zvi Nitzan, Petah-Tikva, Israel

[73] Assignee: Elan Pharma International Limited, County Clare, Ireland

[21] Appl. No.: 08/997,388

[22] Filed: Dec. 23, 1997

Related U.S. Application Data

[60] Provisional application No. 60/034,363, Dec. 26, 1996, provisional application No. 60/036,514, Jan. 28, 1997, and provisional application No. 60/054,647, Aug. 4, 1997.

[30] Foreign Application Priority Data

Jul. 30, 1997 [IE] Ireland ..................................... 970557

[51] Int. Cl.[7] ....................................................... A61N 1/30
[52] U.S. Cl. .............................................. 604/20; 607/152
[58] Field of Search ................................ 604/20; 607/152

[56] References Cited

U.S. PATENT DOCUMENTS

| | | |
|---|---|---|
| 1,033,867 | 7/1912 | Blenkner et al. . |
| 1,899,770 | 2/1933 | Oppenheimer . |
| 2,210,618 | 8/1940 | De St Cyr . |
| 2,469,771 | 5/1949 | Jeppson . |
| 2,716,981 | 9/1955 | More . |
| 3,279,468 | 10/1966 | Le Vine . |
| 3,298,368 | 1/1967 | Charos . |
| 3,447,537 | 6/1969 | King . |
| 3,971,387 | 7/1976 | Mantell . |
| 4,211,222 | 7/1980 | Tapper . |
| 4,248,247 | 2/1981 | Ware et al. . |
| 4,317,457 | 3/1982 | Guillot . |
| 4,365,634 | 12/1982 | Bare et al. . |
| 4,474,570 | 10/1984 | Ariura et al. ............................. 604/20 |
| 4,522,211 | 6/1985 | Bare et al. . |
| 4,580,339 | 4/1986 | Ioffe . |
| 4,655,232 | 4/1987 | Ficke . |
| 4,725,263 | 2/1988 | McNichols et al. . |
| 4,736,752 | 4/1988 | Munck et al. ........................... 128/798 |
| 4,763,660 | 8/1988 | Kroll et al. . |
| 4,867,166 | 9/1989 | Axelgaard et al. . |
| 4,883,457 | 11/1989 | Sibalis ..................................... 604/20 |
| 5,038,796 | 8/1991 | Axelgaard et al. . |
| 5,067,478 | 11/1991 | Berlant . |
| 5,070,862 | 12/1991 | Berlant . |

(List continued on next page.)

FOREIGN PATENT DOCUMENTS

| | | | |
|---|---|---|---|
| 0 060 452 | 9/1982 | European Pat. Off. ......... | A61N 1/30 |
| 0 337 642 | 10/1989 | European Pat. Off. ......... | A61N 1/30 |
| 0 617 979 A1 | 10/1994 | European Pat. Off. ......... | A61N 1/30 |
| 4028125 | 7/1991 | Germany .......................... | A61N 1/30 |
| 2177 928 | 2/1987 | United Kingdom ............. | A61N 1/30 |
| 2239 803 | 7/1991 | United Kingdom ............. | A61N 1/30 |
| WO 92/04937 | 4/1992 | WIPO .............................. | A61N 1/30 |
| WO 92/17239 | 10/1992 | WIPO .............................. | A61N 1/30 |
| WO 94/17853 | 8/1994 | WIPO .............................. | A61N 1/30 |
| WO 96/10440 | 4/1996 | WIPO .............................. | A61N 1/30 |
| WO 92/04937 | 4/1997 | WIPO .............................. | A61N 1/30 |
| WO 96/30077 | 10/1997 | WIPO .............................. | A61N 1/30 |

*Primary Examiner*—Wynn Wood Coggins
*Assistant Examiner*—Eric Kline
*Attorney, Agent, or Firm*—Kathleen L. Maher

[57] ABSTRACT

The invention is directed to a device for delivering a pharmaceutically active compound or cosmetic substance to a subject comprises a flexible substrate sheet attached to an electronic controller. The controller is provided with a pair of electrical contacts on the underside thereof and is adhered to the sheet by means of a pair of strips of electrically conductive adhesive. The underside of the sheet is printed in two halves with electrically conductive ink to provide a pair of electrodes separated by an insulating barrier. A protuberance extends from each electrode and is folded onto the top of the sheet such that the contacts of the controller are adhered in electrical connection with the protuberances and thus also with the electrodes. The use of an adhesive to connect a controller in electrical communication with the electrodes enables an extremely simple construction of delivery device to be achieved.

21 Claims, 13 Drawing Sheets

6,157,858

U.S. PATENT DOCUMENTS

| | | |
|---|---|---|
| 5,085,227 | 2/1992 | Ramon . |
| 5,160,316 | 11/1992 | Henley . |
| 5,169,384 | 12/1992 | Bosniak et al. . |
| 5,246,418 | 9/1993 | Haynes et al. . |
| 5,310,403 | 5/1994 | Haynes . |
| 5,352,315 | 10/1994 | Carrier et al. . |
| 5,356,632 | 10/1994 | Gross et al. . |
| 5,405,317 | 4/1995 | Myers et al. . |
| 5,431,625 | 7/1995 | Fabian et al. . |
| 5,443,441 | 8/1995 | De Clavier . |
| 5,496,363 | 3/1996 | Burgio et al. . |
| 5,498,235 | 3/1996 | Flower . |
| 5,499,967 | 3/1996 | Teillaud et al. . |
| 5,523,090 | 6/1996 | Znaiden et al. . |
| 5,527,357 | 6/1996 | Springer, Jr. . |
| 5,792,097 | 11/1998 | Reddy ...................................... 604/20 |

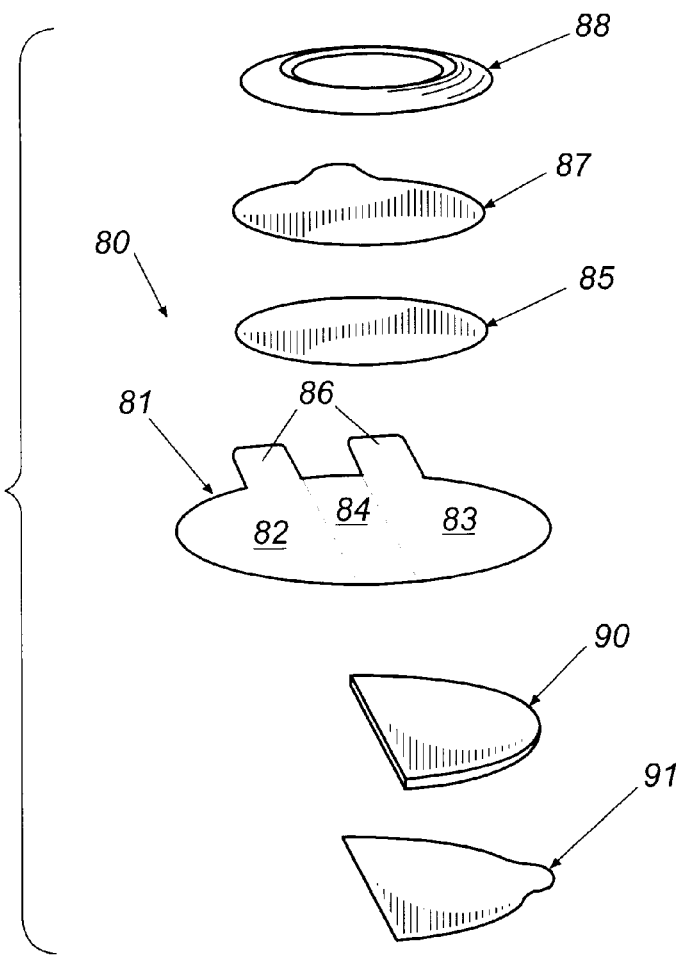
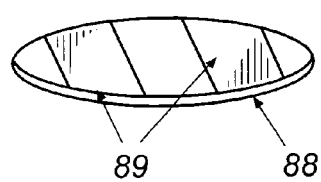
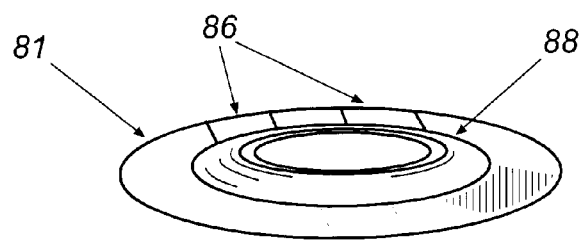
Fig. 13
Fig. 14
Fig. 15

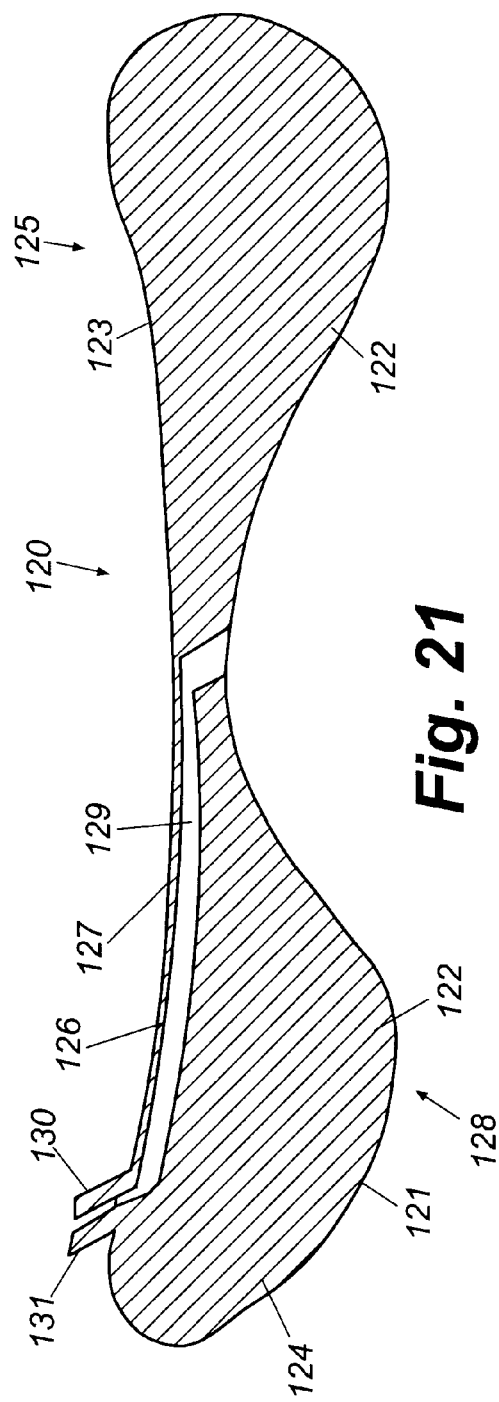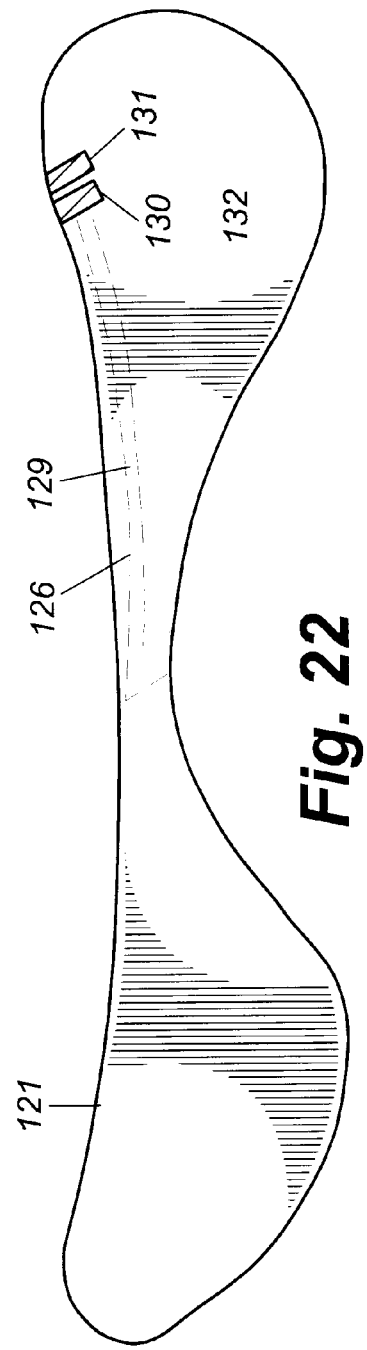

DEVICE FOR THE DELIVERY OF A SUBSTANCE TO A SUBJECT AND IMPROVED ELECTRODE ASSEMBLY

This application claims the benefit of U.S. Provisional No. 60/034,363 filed Dec. 26, 1996, Provisional No. 60,036,514 filed Jan. 28, 1997 and Provisional No. 60/054,647, filed Aug. 4, 1997.

TECHNICAL FIELD

This invention relates to devices for the delivery of a substance to a subject, and in particular to devices for the delivery of a substance via the skin of a subject.

BACKGROUND ART

Typical modes of delivery via the skin of a subject include transdermal, iontophoretic, intradermal, subcutaneous, intravenous and intramuscular delivery.

In many cases where a substance is to be delivered at a controlled rate, the device requires electronic controlling circuitry and delivery or driving means for effecting delivery, under the influence of the controlling circuitry, of the substance from a reservoir to the subject.

The prior art includes a number of devices in which the electronic controller is reusable and the reservoir and delivery means are disposable. This enables the more expensive electronic components to be re-used on a number of occasions, with the disposable part being replaced as the supply of substance becomes exhausted.

In general, the two parts of such devices are provided in separate housing elements which are adapted to connect together by means of a snap-fit connection, for example. A problem associated with such devices is that they are unsuitable for applying a substance such as a medicament or a cosmetic substance to a large area of skin since it is difficult to design a housing which conforms to a large area of skin for a range of subjects, particularly if a degree of mobility is required while the device is in place.

A further disadvantage associated with such devices is the cost associated with designing and manufacturing the components of a housing which must fit together reliably.

The present invention aims to provide a device which overcomes these problems and which is significantly simpler in design and thus less expensive and easier to manufacture, as well as being more user friendly, than known devices.

DISCLOSURE OF INVENTION

The invention provides a device for the delivery of a substance to a subject, comprising:

a) a first part which comprises means for controlling the delivery of a substance to a subject;

b) a second part which comprises electronically controllable delivery means for the delivery of a substance from a supply thereof to a subject;

c) adhesive means for adhering said first and second parts to one another; and d) coupling means adapted to effect communication between the controlling means of the first part and the delivery means of the second part when said first and second parts are affixed to one another by said adhesive means.

The use of adhesive means to effect a mechanical connection between the two parts of the device while also ensuring that the coupling means is engaged, allows an extremely simple construction to be availed of.

Furthermore, since no rigid connection is required, one or both parts can be made of flexible material(s) to enable the device to conform to the skin of a subject over as large an area as is required.

Suitably, the delivery means may be adapted to effect transdermal, iontophoretic, intradermal, subcutaneous, intravenous or intramuscular delivery.

Preferably, said coupling means comprises a set of electrical contacts, at least one contact being disposed on the first part in communication with the controlling means, and at least one contact being disposed on the second part in communication with the delivery means.

More preferably, the first and second parts are each provided with at least two contacts.

The two contacts on each part are suitably positive and negative (or neutral) contacts.

Preferably, said adhering means comprises an electrically conductive adhesive surface provided on at least one of said electrical contacts.

The use of an electrically conductive adhesive surface on an electrical contact reduces the possibility of device malfunction due to a loose contact or to dirty contacts, and thus provides a more reliable device.

Preferably, said adhering means further comprises an electrically insulating adhesive surface provided on the first or second part.

Such an electrically insulating adhesive may be used on its own or in conjunction with an electrically conductive adhesive on the or each electrical contact.

As an alternative to electrical contacts, coupling may be effected indirectly via magnetic fields, such as by induction.

Suitably, the second part is provided with a skin contacting surface, said skin contacting surface being provided with means for retaining the device against the skin of a subject for delivery of said substance to the subject.

Such retaining means is suitably an adhesive on the skin contacting surface.

In preferred embodiments described below, the delivery means is adapted to effect iontophoretic delivery, and at least a portion of said skin contacting surface is electrically conductive and acts in use as an iontophoretic electrode forming part of said delivery means.

Preferably, said skin contacting surface comprises at least two electrically conductive portions which are electrically isolated from one another, each of said portions acting in use as an iontophoretic electrode forming part of said delivery means.

The electrical isolation may be achieved using an insulating portion of the skin contacting surface which may be provided with adhesive to aid retention of the second part on the skin of the subject.

Suitably, said second part is sufficiently flexible to conform to the skin of a subject.

In preferred embodiments, said second part consists essentially of a substrate of flexible material on which the or each electrically conductive portion is deposited.

The use of an adhesive to retain the first and second parts enables such flexible materials to be used which are more lightweight and less cumbersome for the user.

Preferably, the deposition of said electrically conductive portion is effected by printing with conductive ink.

Alternatively, the deposition of said electrically conductive portion may be effected by vapour deposition of a metal.

In preferred embodiments described below, said coupling means comprises a section of the or each electrically conductive portion of the lower surface of the flexible sheet which is folded to expose an electrically conductive contact at the face of the sheet opposite the skin-contacting surface.

This arrangement allows for a simple construction, minimising on components and thus also on costs of manufacture.

Suitably, the or each folded section of the or each electrically conductive portion is adhered to the surface of the sheet opposite the skin contacting surface so as to maintain the or each folded section in position.

Preferably, in such a case, the adhesive means for adhering said first and second parts to one another is also used for adhering the or each folded section to the surface of the sheet opposite the skin contacting surface.

Preferably, two electrically conductive portions, each having a folded section, are employed in the delivery means, said folded sections being folded onto a substantially circular adhesive layer disposed on the surface of the sheet opposite the skin contacting surface.

Further, preferably, one of said folded sections terminates at the periphery of said circular area, and the other of said folded sections extends past the periphery of said circular area towards the centre thereof, said other folded section being provided with an insulating section at the periphery of said circular area, whereby two electrical contacts are provided on said second part, one at the periphery of said circular area and the other towards the centre of said circular area.

The advantages of this arrangement are illustrated and explained below.

Suitably, where iontophoretic delivery is employed, the substance is provided as a semi-solid or mucilaginous coating on said skin-contacting surface.

Examples of such coatings include creams, pastes and gels.

Preferably, said semi-solid or mucilaginous coating is supplied separately from said second part and is applied thereto before use.

This makes an individual device more versatile since it may be used for the delivery of a range of substances, whether proprietary formulations already available in a suitable format or preparations particularly made for delivery with the device according to the invention.

The controlling means may be programmable to optimise the delivery of a particular substance, or it may be pre-programmed with one or more delivery modes chosen on the basis of the ionic nature of the substance to be delivered, the molecular weight of the substance, the required delivery rate, the length of delivery, and whether AC or DC delivery current is most suitable, among other factors.

Suitably, the delivery means comprises a delivery needle extending in use from said skin contacting surface. This arrangement is adapted for intradermal, subcutaneous, intravenous and intramuscular delivery.

In preferred embodiments of the invention, the first part comprises a housing having electrical contacts on a surface thereof for application to the second part.

In a particularly preferred embodiment said housing is substantially circular, and one of said electrical contacts on said housing defines a peripheral region and another of said contacts defines a central region, said contacts being separated by an annular region.

This arrangement of contacts is particularly adapted for use with the arrangement of central and peripheral contacts on a circular adhesive area of the second part, as described above, since it enables the first part to be mounted directly onto the circular adhesive area and ensures a good electrical contact irrespective of the rotational orientation of the first part.

In alternative arrangements, the first part comprises an electronic control unit having at least one lead extending therefrom to a contact for attachment to said second part.

As indicated above, the delivery means may be adapted to effect iontophoretic delivery, at least a portion of the skin contacting surface being electrically conductive and acting in use as an iontophoretic electrode forming part of said delivery means.

Suitably, in such cases, one of the electrodes is an active electrode communicating with the supply of substance and the other of said electrodes is a counter electrode, the controlling means being connected via the adhesive means to the counter electrode.

The controlling means may also be connected via adhesive means to said active electrode or it may be connected to the active electrode other than by adhesive means.

Suitably, said controlling means comprises an electronic circuit adapted to generate an alternating voltage.

Preferably, said voltage alternates with a period of from about 20 seconds to about 10 minutes.

More preferably said voltage alternates with a period of from about 1 minute to about 5 minutes.

This timescale has been found to provide good delivery rates without leading to an overloading of substance in the area of skin immediately below the electrode. It will be appreciated that for individual substances and individual delivery rates or regimes, alternative periods may be suitable, or direct current delivery mode may be preferable.

Preferably, said alternating voltage defines a substantially square waveform having a sawtooth component during the transition between polarities.

The sawtooth component eliminates abrupt transitions between polarities and this has been found to make the device more comfortable for users as it eliminates the "tingling" sensation sometimes associated with AC iontophoretic delivery. Typically, the time taken for the transition between polarities is of the order of 0.1–10 seconds, preferably 0.5–5 seconds.

In a further aspect the invention provides an improved electrode assembly comprising:

a) a flexible substrate having a first surface and a second opposed surface;

b) a pair of spaced apart electrodes applied to the first surface of the substrate;

c) a tab extending from each electrode comprised of electrically conductive material; and d) a power source located within a housing having a pair of spaced apart electrical contacts located on the bottom surface of the housing;

whereby the tabs are folded over onto the opposed surface of the substrate and the power source is fixed to the opposed surface so that each electrical contact is in electrical communication with one of the tabs.

BRIEF DESCRIPTION OF DRAWINGS

The invention will be further illustrated by the following description of embodiments thereof, given by way of example only with reference to the accompanying drawings, in which:

FIG. 13 is an exploded perspective view of a fifth device according to the invention;

FIG. 14 is a perspective view of the underside of the first part of the device of FIG. 13;

FIG. 15 is a perspective view of the device of FIG. 13, when fully assembled;

MODES FOR CARRYING OUT THE INVENTION

Figures 1, 2:
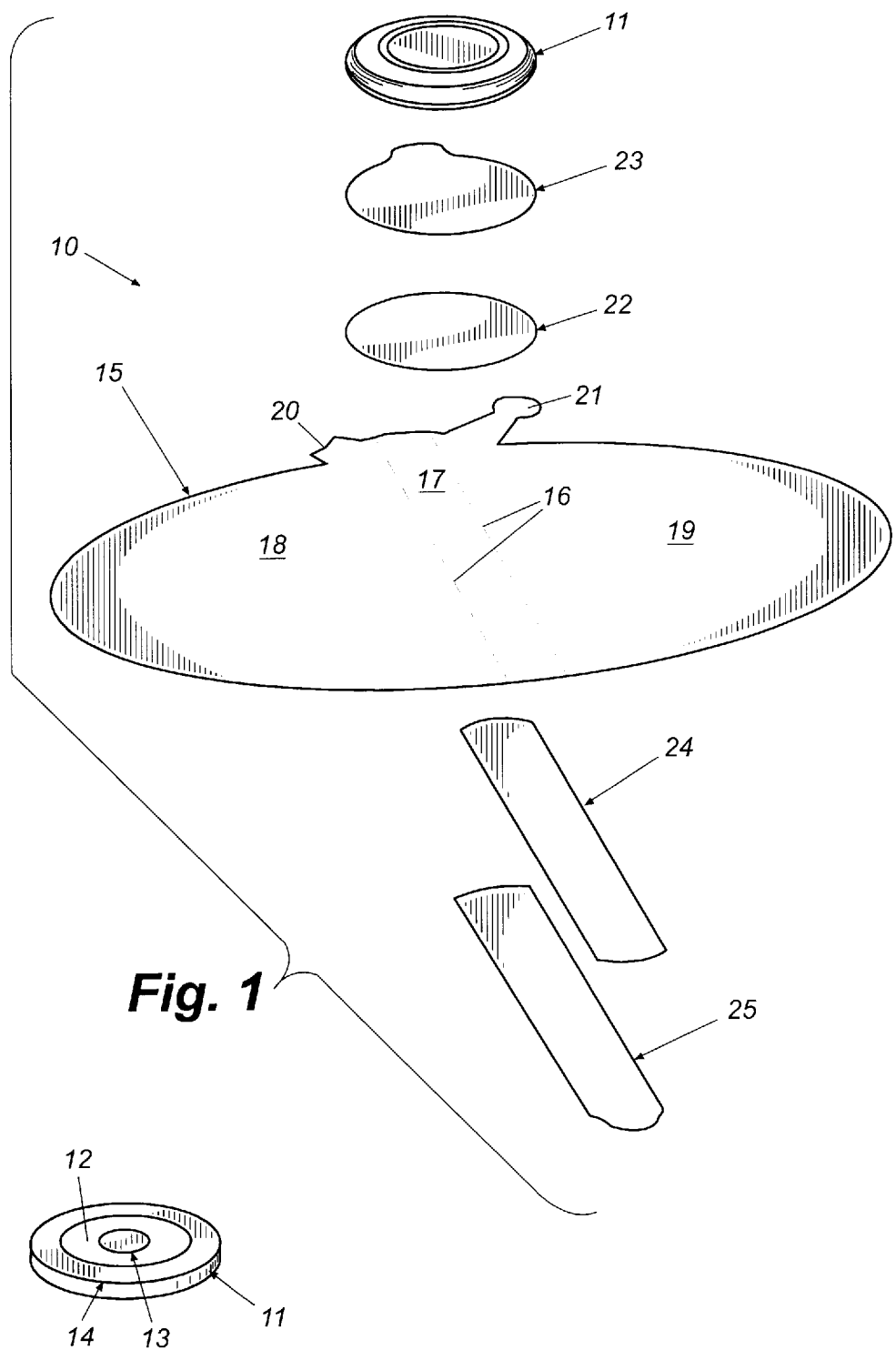
FIG. 1 is an exploded perspective view of a first device according to the invention.
FIG. 2 is a perspective view of the underside of the first part of the device of FIG. 1.

In FIG. 1 there is indicated, generally at 10, an exploded view of a device according to the invention. The device 10 comprises a first part 11 which includes a battery and associated circuitry (described below in relation to FIGS. 16 and 17) for generating and maintaining a predetermined current profile when connected to delivery means. FIG. 2 shows the underside 12 of first part 11, on which a pair of concentric metallic contacts, namely a central contact 13 and an annular contact 14, are disposed.

Referring back to FIG. 1, there is also shown a flexible substrate 15 of insulating material such as hygienic non-woven tissue paper. A suitable tissue paper is a 60 grade tissue paper made by EFAR of Tiberius, Israel. The underside (not visible) of sheet 15 is coated with a food grade lacquer and this lacquer in turn is coated with an electrically conductive coating using conductive ink. A suitable conductive ink is made by adding, to a conductive ink (available from Sipca of Switzerland) an amount of carbon powder sufficient to provide the required conductivity. Suitable carbon powder includes "Super P" carbon powder manufactured by M. M. M. Carbon of Willebrock, Belgium.

A central strip, denoted by dotted lines 16, on the underside of sheet 15, is not printed with conductive ink, thus leaving an insulating barrier 17 between two halves 18,19 of the conductive underside.

The sheet 15 is shaped such that a short tab 20 and a long tab 21 project from the edge of the sheet 15. Short tab 20 projects from half 18, and long tab 21 projects from half 19 of the sheet 15. The conductive coating on the underside of each half 18,19 extends to the underside of each of the tabs 20,21, and the tabs 20,21 are electrically isolated from one another by insulating barrier 17.

As shown in the exploded view of FIG. 1, a circular layer of electrically insulating adhesive 22 is located above sheet 15 adjacent the tabs 20,21. A circular release liner 23 is provided above insulating adhesive 22.

As also shown in FIG. 1, a longitudinal layer of electrically insulating adhesive 24 is located below the insulating barrier 17 of sheet 15 and a longitudinal release liner 25 is provided below insulating adhesive 24.

Figure 3:
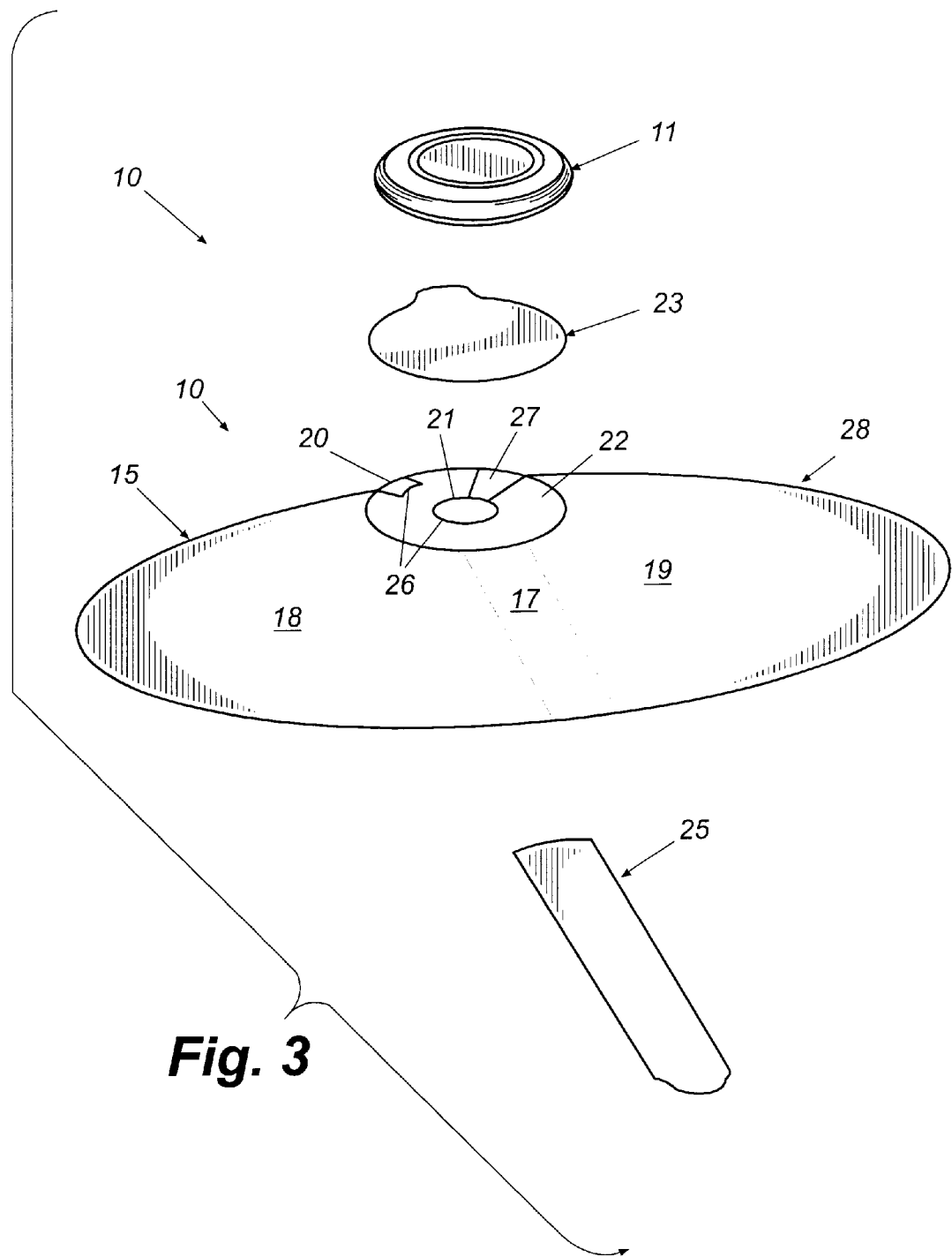
FIG. 3 is a further exploded perspective view of the device of FIG. 1, with some components assembled together.

FIG. 3 shows the device 10 in a more advanced state of assembly, with adhesive layer 22 positioned on sheet 15 and the tabs 20,21 folded onto adhesive layer 22 such that the conductive ink coating 26 is uppermost. Long tab 21 is provided with an insulating coating 27 over part of its surface. Release liner 23 is affixed on top of the adhesive layer 22 and the exposed tab surfaces.

The longitudinal layer of insulating adhesive 24 shown in FIG. 1 (not visible in FIG. 3) is positioned on the underside of sheet 15 covering the barrier 17, and longitudinal release liner 25 is affixed to the longitudinal adhesive layer 24 at the final stage of manufacture.

The device 10 is supplied to users with the release liners 23,25 in place, and the first part 11 separate from the second part 28 (second part 28 being the assembly comprising sheet 15 and adhesive layers 22,24).

In use, the device 10 is adapted to deliver a therapeutic or cosmetic agent to the skin of a subject. The substance to be delivered is suitably provided as a cream and is coated on the underside of sheet 15 so as to substantially cover the underside of sheet 15. Release liner 25 is then peeled away so that the central adhesive strip 24 is free of cream but the two halves on either side are covered by the cream which contains the substance for delivery. Sheet 15 is then applied to the area of skin to be treated, with the cream between the skin and the sheet 15.

Preferably, such cosmetic agents include vitamin A and/or vitamin E, or alpha hydroxy acid; and a medicinal agent may include tetracycline, other antibiotics, anti-acne medicaments or anti-toxins.

To reduce cellulite deposits, a user would apply an agent used to reduce cellulite deposits such as caffeine extract, theophylline extract, ginkgo extract, silisium, magnesium, and/or gola.

Applicant also anticipates that agents used in this invention may include those used to treat skin disorders. Agents applied to the skin to treat such disorders include but are not limited to vitamin A, vitamin E, anti-fungal agents and alpha hydroxy acid. Moreover, it is further anticipated that the present invention would also include devices and methods for treating skin disorders of the feet, toes and toe nails. These include but are not limited to athlete's foot medicament, anti-fungal agents and skin moisturizers.

Applicant further anticipates similar application of the present invention to treat scalp disorders such as psoriasis, and baldness. Agents used in the treatment of head and scalp disorders include: minoxidil, anti-dandruff agent and anti-psoriasis medicament. It is also anticipated that the present invention be applied to the skin surface of the penis to treat male impotency. Agents used in the treatment of male impotency include penile erection stimulants such as prostaglandin. The examples of use of this invention to treat certain disorders are by way of example and are not meant to limit the scope of the present invention. It is anticipated that the present invention have numerous applications to a variety of body parts to treat a number of different ailments.

Figure 6:
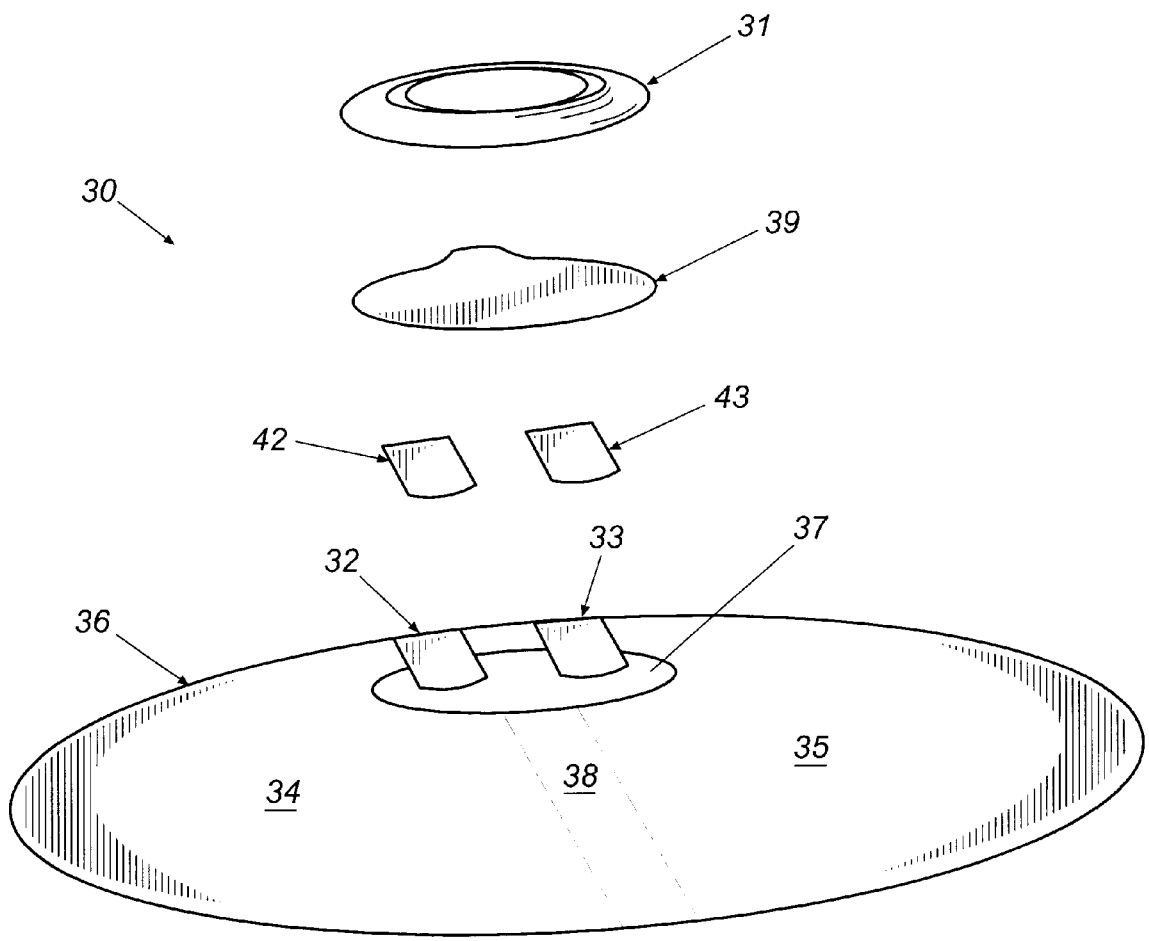
FIG. 6 is a partially exploded perspective view of the device of FIG. 5.

Preferably, the electrical current used in the present invention is direct current, applied in sessions of alternating polarity. In this way, the chemicals of the lotion are driven in one direction by the electrical current of the entire duration of a session, and in the opposite direction for the entire direction of the subsequent session. In addition, alternating the polarity of the sessions prevents undesirable electrolysis within the skin tissue. FIG. 6 shows a preferred current waveform. Note that the electrical current is ramped on, i.e., increases gradually from zero to a maximum value, and then ramped off, i.e., decreases gradually back to zero, to prevent irritation associated with a sudden onset of current. The preferred electrical current density is between about 50 microamperes per square centimeter and about 500 microamperes per square centimeter, to effectively reduce the cellulite without irritating or burning the skin. The preferred pulse duration is between about 30 seconds and about 120 seconds for each period of full current, with ramp duration, from zero current to full current or from full current to zero current, of about one second.

While the invention has been described with respect to a limited number of embodiments, it will be appreciated that many variations, modifications and other application of the invention may be made. For example, the substrate may be made of a thin flexible inexpensive material other than tissue paper, such as cloth or polyester sheet. It is also anticipated that at least one electrode having varied resistance may be made of a molded elastomer. The electrode would be molded in the shape of a human extremity such as a finger, or toe so as to be slipped onto the finger, toe or the like for treatment of skin or nail disorders or the like. Moreover, the lower layers may be made of other conductive materials such as metallic sheet or foil. In addition, it is anticipated that the lacquer and conductive materials may be applied to the base 10 by means other than silk screening, such as rotor gravure printing, laser printing, stenciling, lamination, extrusion and other means commonly known in the art.

Figure 4:
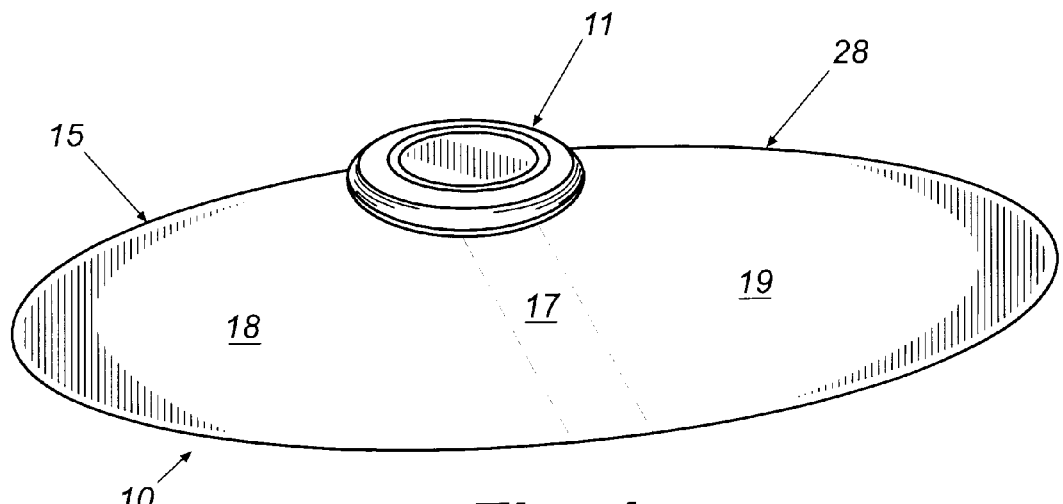
FIG. 4 is a perspective view of the device of FIG. 1, when fully assembled.

Circular release liner 23 is removed, thereby exposing circular adhesive layer 22 and the conductive surfaces 26 of the short and long tabs 20,21. Circular adhesive layer 22 is designed to hold first part 11 in contact with the conductive surfaces 26. Referring additionally to FIG. 2, it can be seen that when first part 11 is applied to the circular adhesive layer 22 (as shown in FIG. 4), central contact 13 (FIG. 2) contacts the conductive surface 26 (FIG. 3) of long tab 21, and annular contact 14 (FIG. 2) contacts the conductive surface 26 (FIG. 3) of short tab 20.

An iontophoretic electrical circuit may thus established from the central contact 12 to the annular contact 14 of first part 11 via the skin of the subject. The iontophoretic circuit utilises the cream-coated conducting underside of one half of the sheet 15 as a working electrode and the cream-coated conducting underside of the other half of the sheet 15 as a counter electrode. The principles of such iontophoretic delivery are well known to those skilled in the art.

By employing suitable circuitry in first part 11, the direction of flow of current can be arranged to alternate such that each half 18,19 of the underside of sheet 15 repeatedly alternates between acting as the working electrode and the counter electrode. This reduces the likelihood of burns, and enables one to effectively utilise the entire area of the sheet 15 for delivery of the substance (apart of course from the small area of the insulating barrier 17 which separates the two halves 18,19).

The advantages of the device 10 can be appreciated in that it is lightweight, inexpensive, and extremely easy to apply. The method of attaching the electronic controller of first part 11 to the electrode sheet 15 of second part 28 is particularly advantageous, since by simply applying the first part 11 onto the contact adhesive 22, the necessary electrical connections are automatically made and the device is ready for delivery of drug.

Figure 5:
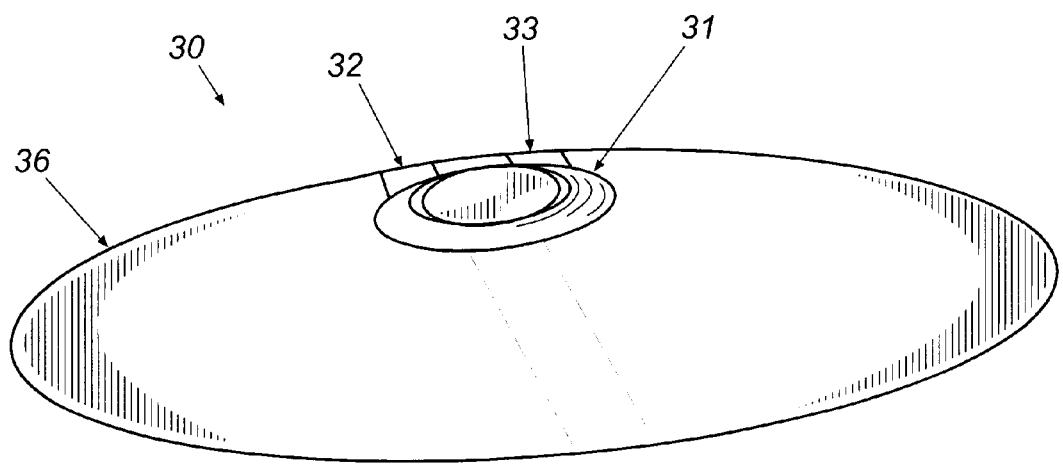
FIG. 5 is a perspective view of a second device according to the invention, when fully assembled.

FIG. 5 shows a device, indicated generally at 30, which is essentially similar to device 10 of FIGS. 1–4, but differs in certain respects. It can be seen that instead of employing central and annular contacts, the first part 31 of device 30 is in contact with a pair of parallel tabs 32,33 which effect contact with the two conductive halves 34,35 of the underside (not shown) of the sheet 36.

FIG. 6 shows the device 30 in partially exploded view, with a circular insulating adhesive layer 37 already in place on sheet 36, and with tabs 32,33 already folded over onto circular adhesive layer 37. Similarly, a longitudinal insulating adhesive layer (not shown) is already positioned on the underside of insulating barrier 38 along the gap between the conductive halves 34,35 of the underside of sheet 36. A release liner (not shown) is provided over the longitudinal adhesive strip (as in the device of FIG. 1–4) and a circular release liner 39 is provided to cover the circular adhesive layer 37.

Figure 7:
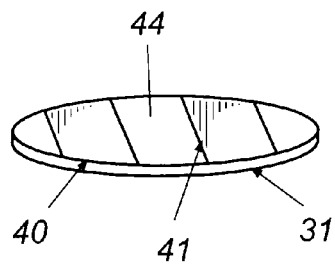
FIG. 7 is a perspective view of the underside of the first part of the device of FIG. 5.

FIG. 7 shows the underside of first part 31 of device 30, from which it can be seen that two parallel contacts 40,41 are dimensioned to contact the parallel conductive tabs 32,33 of sheet 36. Unlike the first part 11 of device 10 (see FIG. 2), first part 31 of device 30 should be oriented correctly to ensure good contact between the contacts 40,41 and the conductive tabs 32,33. However, by choosing a suitable geometry for the tabs and contacts, such difficulties are easily avoided.

A further point of difference from the device 10 of FIGS. 1–4 is that a pair strips of electrically conductive adhesive 42,43 are disposed on top of the conductive tabs 32,33, respectively. A suitable conductive adhesive is sold under item no. 021200-67868 by 3M Corporation.

The strips of conductive adhesive 42,43 ensure a better electrical contact between the contacts 40,41 and the conductive tabs 32,33, than is obtained by relying on mechanical contact alone, and ensure a better adhesion since the entire area of the base 44 (FIG. 7) of first part 31 is adhered to the sheet 36, including the electrical contact areas.

Figure 8:
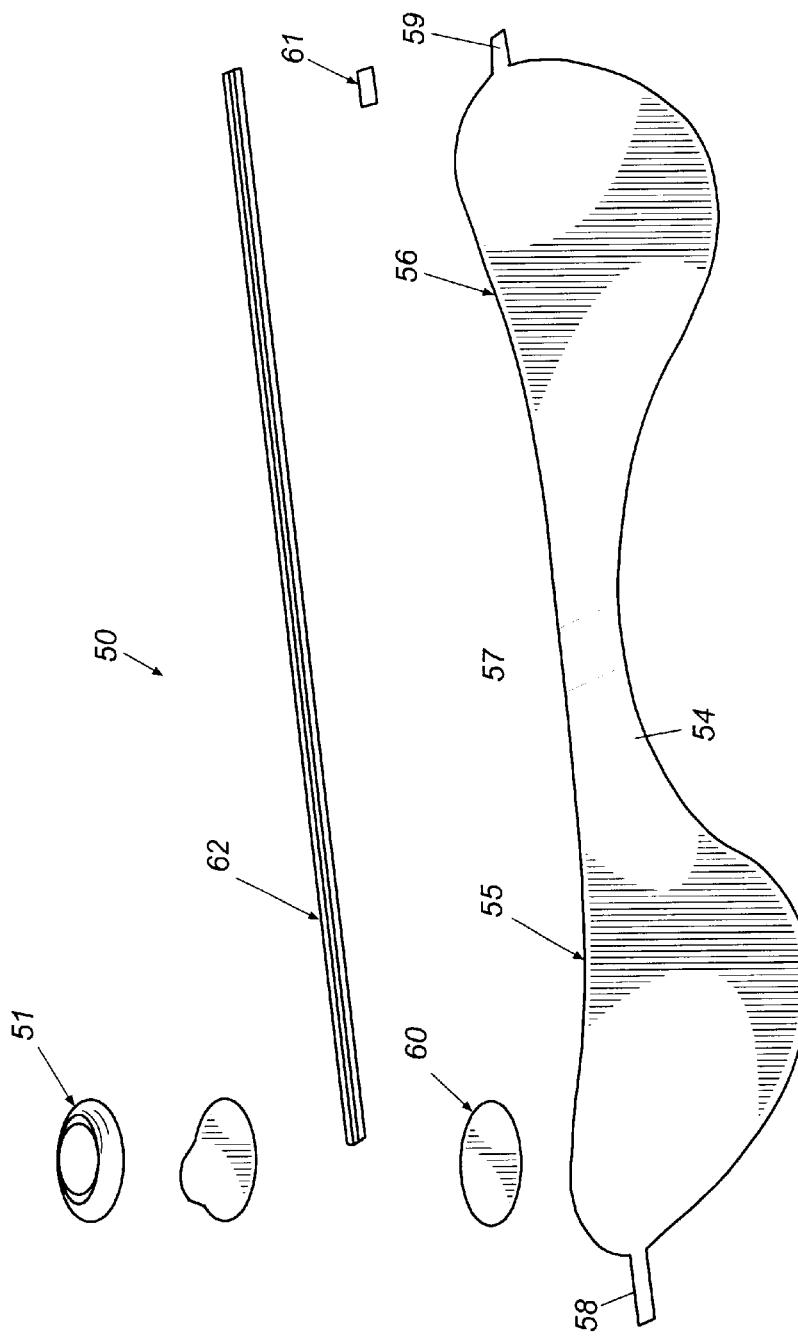
FIG. 8 is a partially exploded perspective view of a third device according to the invention.

FIG. 8 shows a further embodiment of a device according to the invention, indicated generally at 50 in exploded view. Device 50 is particularly adapted for cosmetic use, due to the overall shape of the sheet 54 being suitable for application to the nose and cheek area of the face. In this embodiment, the first part 51 has two contacts 52 (see FIG. 9) which are co-linear and separated by a gap 53.

The tissue paper sheet 54 again has two halves 55,56 the undersides of which are conductive and separated by an insulating barrier 57 between said halves. From each of the halves 55,56 extends a foldable tab 58,59.

A circular insulating adhesive layer 60 is used to hold tab 58 in a folded position such that it presents a conducting surface for contact with the first part. A short adhesive strip 61 holds tab 59 in a folded position, and an elongated conductive strip 62, made of metallised polyethylene sheeting having an adhesive underside, is adhered to sheet 54 such that it extends from tab 59 (with which it is in electrical contact) to circular insulating adhesive layer 60, as shown in FIG. 10.

A release liner 63 provided on circular insulating adhesive layer 60 is removed before use, and as described above, the first part 51 is adhered to the circular insulating adhesive layer, whereby one of the contacts 52 on the underside of first part 51 (see FIG. 9) contacts tab 58 (to thereby make an electrical connection with the conductive coating on the underside of half 55 of sheet 54), and the other of the contacts 52 on the underside of first part 51 (see FIG. 9) contacts strip 62 (to thereby make an electrical connection with the conductive coating on the underside of half 56 of sheet 54).

Figure 10:
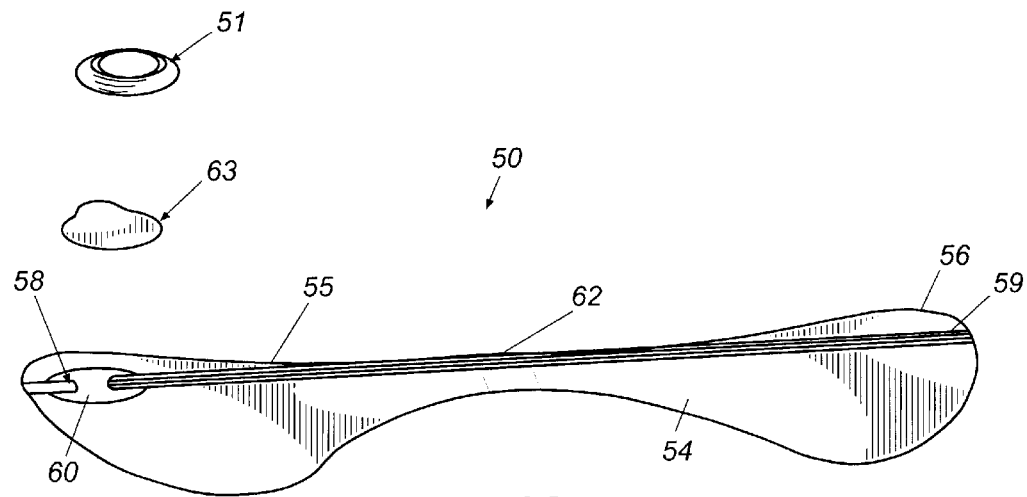
FIG. 10 is a perspective view of the device of FIG. 8, when fully assembled.
Figure 11:
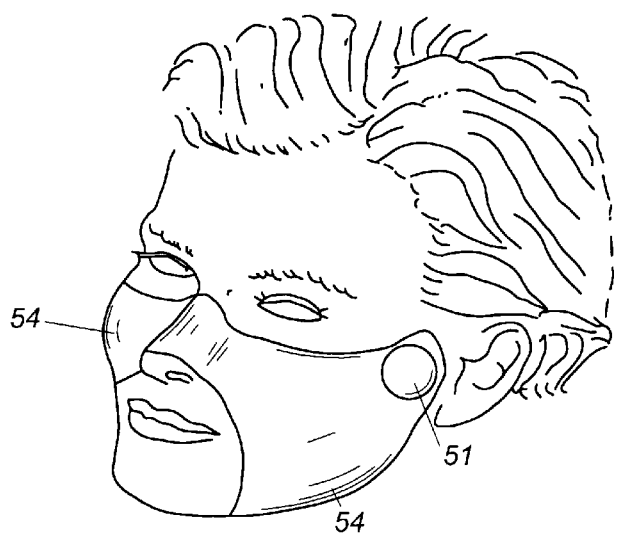
FIG. 11 is a perspective view of the device of FIG. 8, in use.

FIG. 11 is a schematic illustration of the device 50 of FIG. 10 in use, with the sheet 54 in place over the cheeks and nose of a user. Although there is an adhesive strip providing some adhesion along the nose (i.e. an adhesive strip on the underside of insulating barrier 57 (FIG. 8), the main adhesive force occurs naturally by as the underside surface of the sheet 54 covered in a cosmetic cream clings to the skin of the face. The first part 51 can be seen beside the ear of the user.

Figure 12:
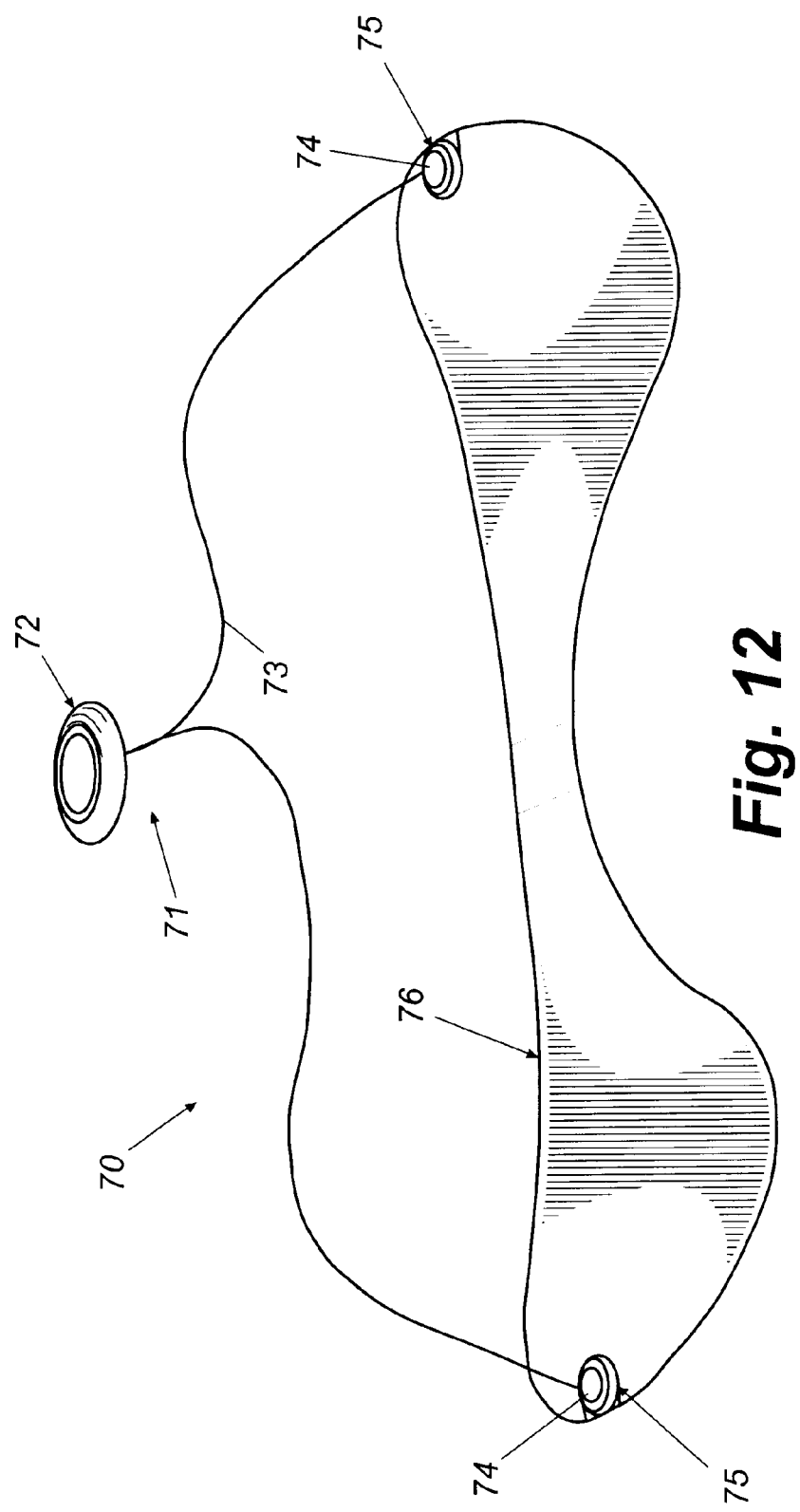
FIG. 12 is a perspective view of a fourth device according to the invention, when fully assembled.

FIG. 12 shows another device according to the invention, indicated generally at 70. This device differs from that of previously described embodiments in that the first part, indicated generally at 71, has an electronic control module 72 connected by wires 73 to a pair of contacts 74.

Each contact 74 is adhered to a folded tab 75 on tissue sheet 76. The tab is maintained in a folded position by an area of insulating contact adhesive (not shown), and the exposed surface of the tab 75 (i.e. the surface to which the contact 74 is attached) is provided with a layer of electrically conductive adhesive (not shown) to effect both adhesion and electrical contact between the contact 74 and the tab 75. When worn on the face, the appearance is similar to that of the device of FIG. 11, apart from the fact that instead of a single electronic controller positioned on the sheet 76, a pair of smaller contacts 74 extend to either edge of the sheet 76, the visual effect being somewhat similar to a person wearing a pair of headphones.

FIG. 13 shows yet a further alternative embodiment which is generally similar to those previously described but is of smaller size. Thus, the device, indicated generally at 80, has a sheet 81 having first and second halves 82,83 the undersides of which are conductive and are separated by an insulating barrier 84. A circular layer of insulating adhesive 85 holds parallel tabs 86 in a folded position and is initially covered by a release liner 87. Before use, release liner 87 is removed and first part 88 of device 80 is adhered to the adhesive 85, with a pair of parallel contacts 89 (FIG. 14) thereby making electrical contact with the folded tabs 86. The device is shown in use in FIG. 15.

FIG. 13 shows a variation on previously described devices, however, in that the underside of second half 83 of sheet 81 is provided with a layer of conductive gel 90 protected before use by a release liner 91. Before use, only the first half 82 of sheet 81 is covered by the substance to be delivered, and thus gel 90 is positioned in use in direct contact with the skin. The electronic controlling circuitry of first part 88 is adapted to deliver a substance by a direct current rather than by an alternating current. This is advantageous in certain cases, since delivery times can be shortened compared to using an alternating current. Thus, first half 82 is a permanent working electrode and second half 83 is a permanent counter electrode.

The device of FIG. 13 was tested using the local anaesthetic preparation marketed by Astra AB of Sweden as "Emla" ("Emla" is a Trade Mark for a mixture of lidocaine (lignocaine) and prilocaine). It can be used as a surface anaesthetic to produce local anaesthesia before procedures such as lumbar punctures, split skin grafting and laser treatment. It is recommended that it be applied under an occlusive dressing for at least 60 minutes before the procedure is carried out, in order for a sufficient degree of anaesthesia to be reached. When "Emla" was delivered using the device of FIG. 13, however, it was found that the same degree of anaesthesia was reached after only 15 minutes as when absorbed passively. This suggests that by enabling iontophoretic devices to be produced in lightweight inexpensive form, the invention makes more attractive the use of iontophoresis in anaesthesia, which in turn allows medical procedures such as those listed above to be shortened and to become less traumatic.

The choice between direct current and alternating current depends on factors such as the nature of the substance to be delivered, and the required delivery rate.

Figure 16:
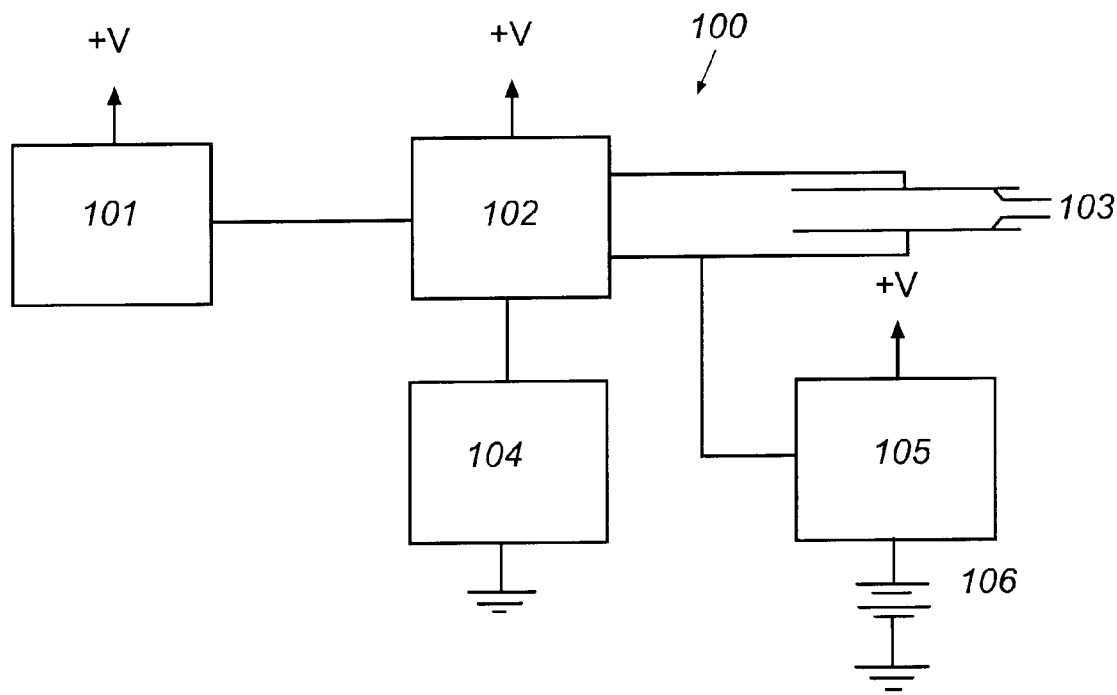
FIG. 16 is a block diagram of a circuit used in the controlling means of a device according to the invention.

FIG. 16 shows a block diagram of a circuit, indicated generally at 100, which is designed for the delivery of a substance using an alternating current. In circuit 100, an oscillator 101 generates signals at equal 60 second periods. These signals are fed to a H bridge 102 which provides a substantially square AC waveform voltage across the electrodes 103. Electrodes 103 in use are placed on the skin of a subject, as described above.

A current stabiliser 104 connected to the H Bridge 102 ensures that the magnitude of current is within predetermined limits, and in particular that the current does not rise above a level which could cause discomfort or skin burns.

An automatic switch 105 connected to a battery 106 which drives the circuit 100 triggers the oscillator 101 and H Bridge 102 by monitoring the flow of current from the battery 106. Before the device is applied to a subject, the circuit 100 is open and no current can flow between the electrodes 103. When the circuit is closed by application of the electrodes 103 to a subject, a small leakage current flows from the battery 106 and this triggers switch 105 to actuate the circuit 100.

Figure 17:
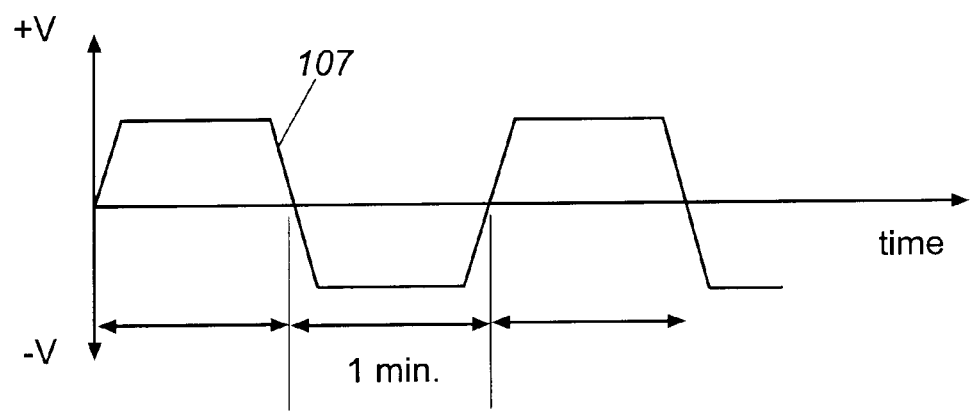
FIG. 17 is a schematic graphical illustration of the voltage waveform produced by the circuit of FIG. 16, shown as voltage plotted against time.

FIG. 17 shows the applied voltage waveform 107 generated by the oscillator 101 and H Bridge 102. Thus, it can be seen that the waveform 107 is substantially square, having a frequency of approximately $8.3 \times 10^{-3}$ Hz or 0.5 cycles/min (i.e. each half cycle lasts 60 seconds before the oscillator triggers the H Bridge to reverse the direction of current flow).

It will be noted, however, that the switch in voltage is not abrupt but has a saw-tooth element during the switch in polarity, and thus there is a finite time taken to change the direction of current flow between the electrodes. This has been found to allow the device to be worn more comfortably by eliminating the "tingling" sensation felt by users as the current direction changes between half-cycles.

Figure 18:
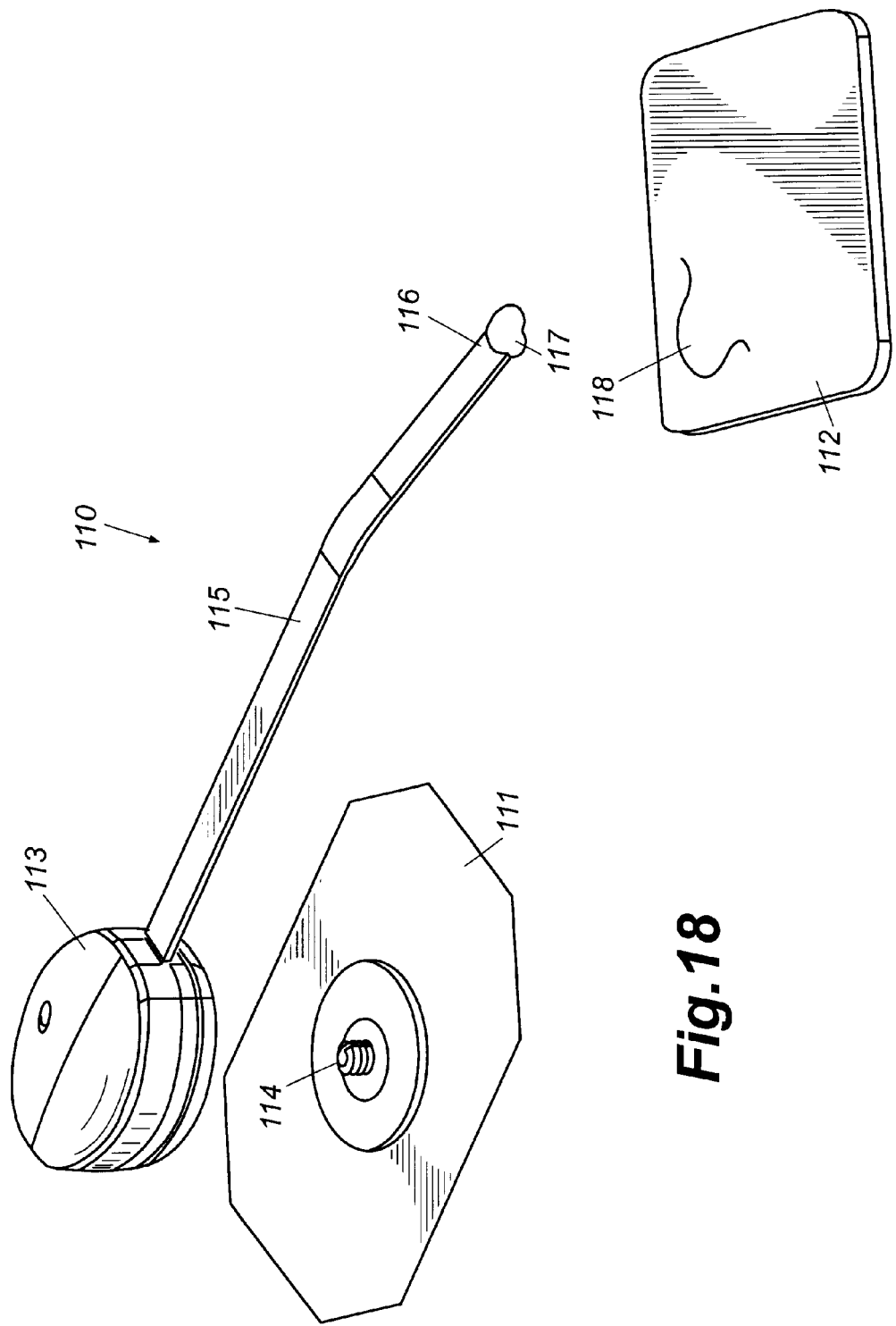
FIG. 18 is a perspective view of a sixth device according to the invention.

FIG. 18 shows a further embodiment of the invention in the form of a device, indicated generally at 110, having an active electrode 111, a counter electrode 112 and an electronic control unit 113. Electronic control unit 113 is mountable on active electrode 111 by means of a snap-fit connection on the underside (not shown) of electronic control unit 113 which mates with a stud 114 mounted on active electrode 111. As well as mechanically connecting active electrode 111 and electronic control unit 113, the stud enables an electrical connection from the electronic control unit 113 to the active electrode 111.

A flexible conductive strip 115 extends from the electronic control unit 113. At its free end 116, strip 115 is provided with a release liner 117 which covers a piece of electrically conductive contact adhesive. Counter electrode 112 has a tab 118 to which the end 116 can be adhered in use to provide an electrical connection between the electronic control unit 113 and the counter electrode 112 in use.

Active electrode 111 is provided on its underside (not shown) with an absorbent sponge material which receives a solution of the substance for delivery immediately prior to use. Counter electrode 112 is a gel electrode such as is well known in the art.

Figure 19:
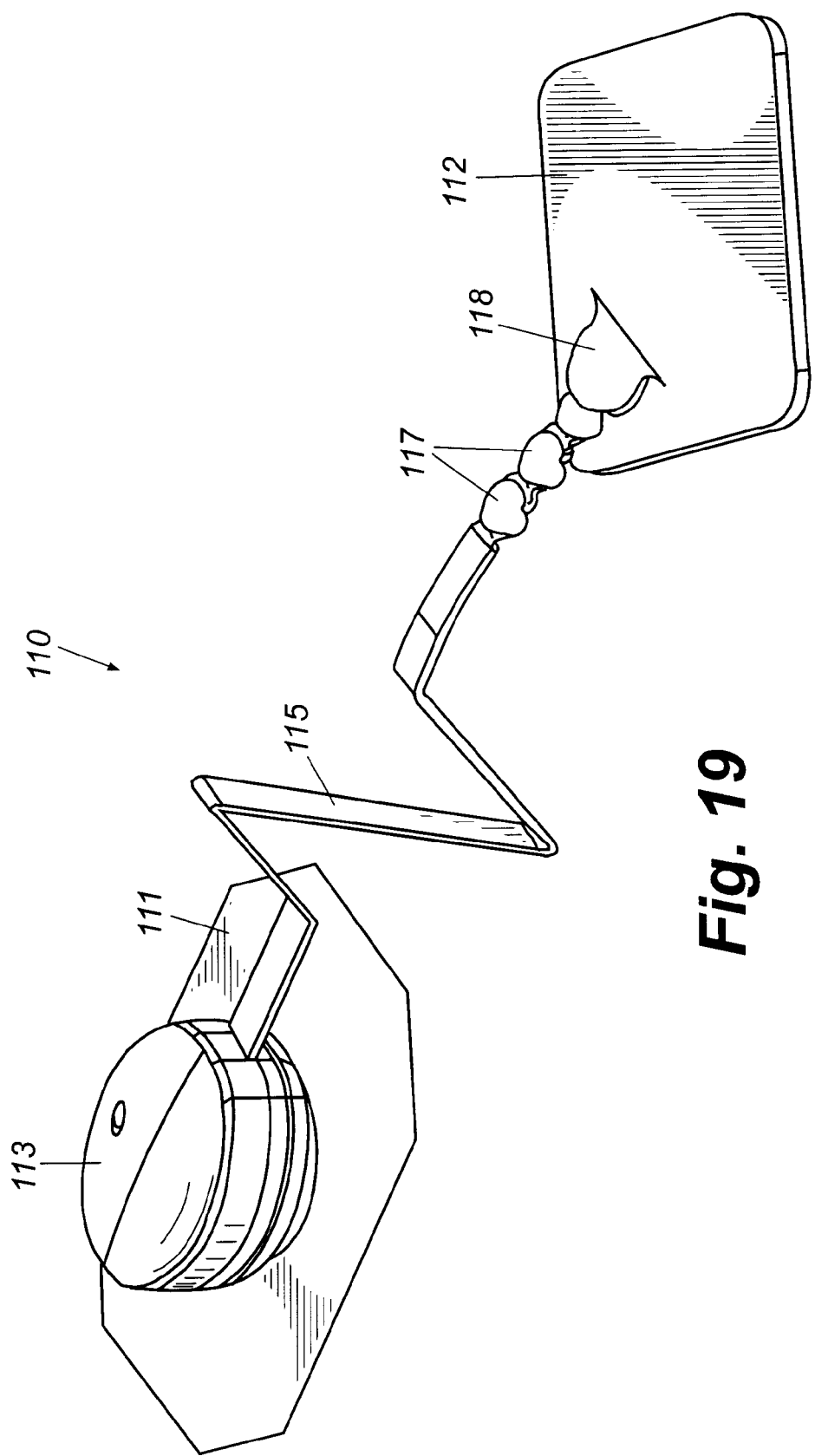
FIG. 19 is a perspective view of a seventh device according to the invention, being a variation on the device of FIG. 18.
Figure 20:
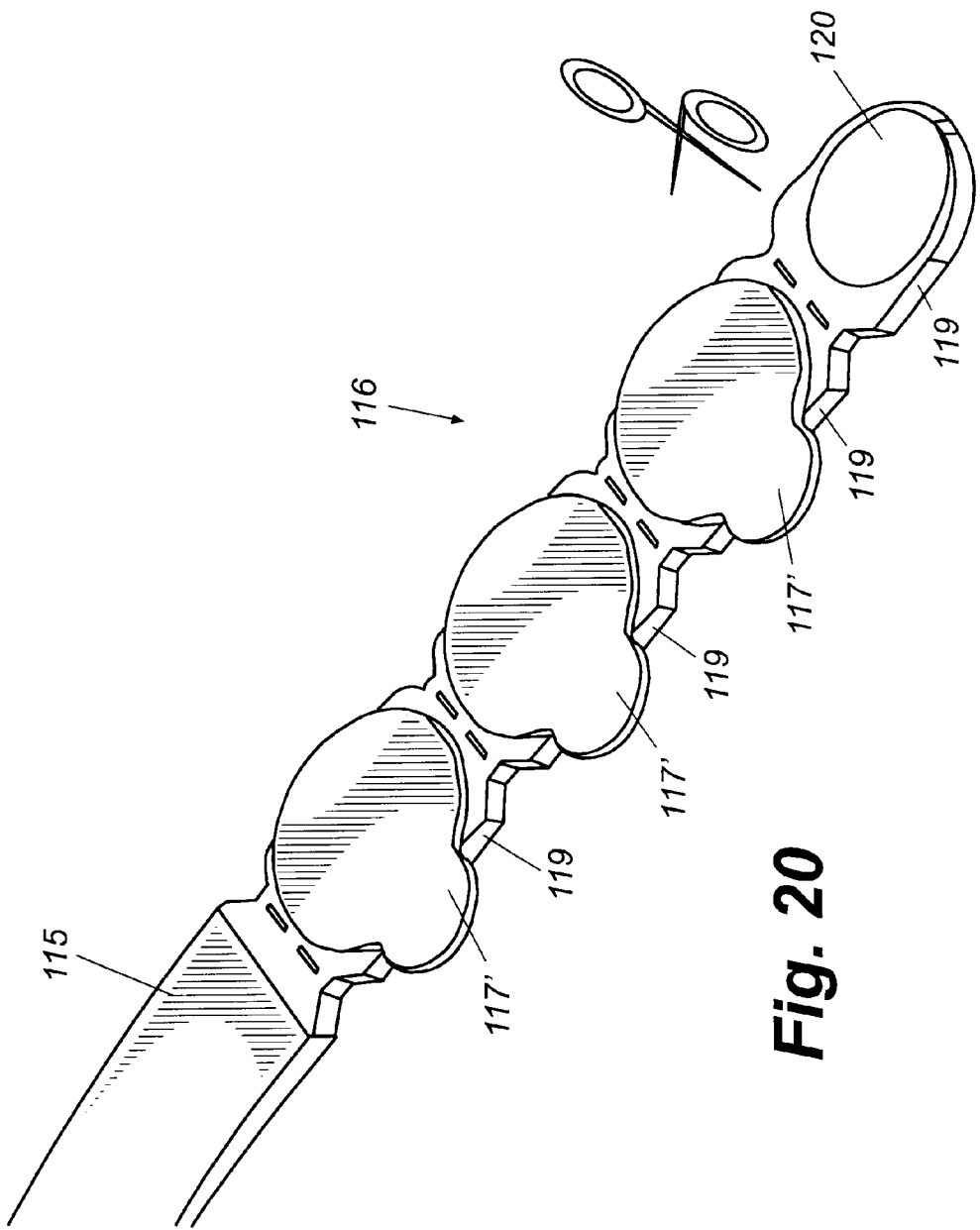
FIG. 20 is a perspective view of a detail of the device of FIG. 19.

FIG. 19 shows a variation on the FIG. 18 embodiment in which like parts are represented by like reference numerals, but in which release liner 117 is replaced by a plurality of release liners 117'. Referring additionally to FIG. 20, the end 116 of strip 115 (FIG. 19) is shown in greater detail. It can be seen that the individual release liners 117' are provided on a series of perforated tear-off (or cut-off) portions 119, each release liner 117' covering a separate spot of electrically conductive contact adhesive 120.

The advantage of this embodiment is that the electronic control unit 113 can be reused a number of times (depending on the life of the battery included inside it), and connected in successive uses to fresh electrodes 111,112. After each use the electronic control unit 113 is snapped away from the active electrode 111 and the end 116 of strip 115 is disengaged from the counter electrode 112 by tearing off the endmost tear-off portion 119. The next time the device is used, the next (and now endmost) release liner 116' is removed and the underlying adhesive pressed against the tab.

Of course there is no reason why the nature of the two electrodes cannot be reversed, with the electronic control unit 113 mounted on a counter electrode and connected by adhesive means to an active electrode.

As a variation on the device of FIG. 18, the strip may be separate from the control unit, and it may be provided at both ends with an adhesive pad. One end of the adhesive pad may then be connected adhesively to an electrical contact point on the control unit and the other end may be connected adhesively to the counter electrode as describe in relation to FIGS. 18–20.

Alternatively, the counter electrode could be supplied with a connecting strip extending therefrom for adhesive connection to a control unit (as opposed to the FIG. 18 embodiment wherein the strip 115 extends from the control unit 113 for adhesive connection to the electrode 112.

Figure 9:
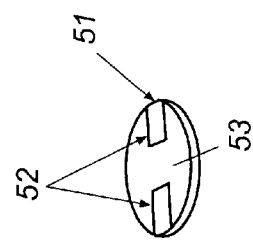
FIG. 9 is a perspective view of the underside of the first part of the device of FIG. 8.

FIG. 21 shows yet a further embodiment of the invention, similar in may respects to the embodiment shown in FIGS. 8–10. In FIG. 21 there is indicated, generally at 120, the underside of a tissue paper sheet 121 printed with conductive ink 122 to form two spaced-apart electrodes 123, 124.

Electrode 123 substantially covers one half 125 of the sheet but extends in a continuous strip 126 along an edge 127 of the other half 128 of the sheet 121. Electrode 124 substantially covers this other half 128 but stops short of the edge 127 so that a gap 129 is present between the electrodes 123, 124. At the end of the strip 126, electrode 123 terminates in a protuberance 130. Electrode 124 is provided with an adjacent protuberance 131.

Referring next to FIG. 22, the top side of tissue paper 121 can be seen, with strip 126 and gap 129 indicated by dotted lines. The tabs 130, 131 are folded over and adhered onto the top surface 132 of sheet 121, providing electrically conductive contacts against which the electronic control unit of FIG. 7 can be adhesively mounted as previously described. The embodiment of FIGS. 20 and 21 is advantageous in that it obviates the necessity of providing a connecting strip (such as the strip 62 shown in FIG. 8), since the printed areas of the electrodes 123, 124 are shaped to make such a strip redundant.

It will be appreciated that the embodiments discussed above are preferred embodiments, falling within the scope of the appended claims, and that various alternative embodiments are contemplated.

What is claimed is:

1. A device for the delivery of a substance to a subject, comprising:
   (a) control means for controlling the delivery of a substance to a subject, comprising a power source and a pair of electrically conductive contacts;
   (b) a substrate having a first surface and a second surface;
   (c) a pair of spaced apart electrodes fixed to the first surface of the substrate for the delivery of a substance from a supply thereof to the skin surface of a subject;
   (d) a pair of electrical couples adapted to affect electrical communication between the conductive contacts of the control means and the spaced apart electrodes when each of the electrically conductive contacts of the control means and the electrodes are affixed to one another, each couple being integral with one of the electrodes and fixed to the first surface of the substrate; and
   (e) adhesive on the second surface of the substrate for adhering the pair of electrically conductive contacts of the control means and the pair of electrical couples to one another, whereby when each of the electrical couples is folded away from itself, electrical communication is made between the pair of electrodes and the power source.

2. A device according to claim 1, wherein the control means comprises an electronic circuit adapted to generate an alternating voltage.

3. A device according to claim 2, wherein the voltage alternates with a period of from about 20 seconds to about 10 minutes.

4. A device according to claim 3, wherein the voltage alternates with a period of from about 1 minute to about 5 minutes.

5. A device according to claim 2, wherein the alternating voltage defines a substantially square waveform having a sawtooth component during the transition between polarities.

6. A device according to claim 1, wherein one of the electrodes is an active electrode communicating with the supply of substance and wherein the other of the electrodes is a counter electrode, the control means being connected via the adhesive to the counter electrode.

7. A device according to claim 6, wherein the control means is also connected via the adhesive to the active electrode.

8. A device according to claim 6, wherein the control means is connected to the active electrode by mechanical means.

9. A device according to claim 1, wherein the adhesive comprises an electrically conductive adhesive surface provided on at least one of the electrical couples.

10. A device according to claim 9, wherein the adhesive further comprises an electrically insulating adhesive surface provided on the electrodes or contacts.

11. A device according to claim 1, wherein the electrical contacts are folded onto a substantially circular adhesive layer disposed on the second surface of the substrate.

12. A device according to claim 11, wherein the first folded electrical contact terminates at the periphery of said circular area, and the the second folded electrical contact extends past the periphery of the circular area towards the center thereof, the second folded section being provided with an insulating section at the periphery of the circular area, whereby the two electrical contacts are provided at the periphery of the circular area and towards the center of the circular area.

13. A device according to claim 1, wherein a semi-solid or mucilaginous coating is provided on the electrode.

14. A device according to claim 13, wherein the semi-solid or mucilaginous coating is supplied separately from the electrode and is applied thereto before use.

15. A device according to claim 1, wherein the electrodes are provided with a skin contacting surface, the skin contacting surface being provided with means for retaining the device against the skin of a subject for delivery of the substance to the subject.

16. A device according to claim 1, wherein the delivery means is sufficiently flexible to conform to the skin of a subject.

17. A device according to claim 1, wherein the electrode is fixed to the first surface of the substrate by printing with conductive ink thereon.

18. A device according to claim 1, wherein the electrode is fixed to the first surface of the substrate by the vapour deposition of a metal thereon.

19. A device according to claim 1, wherein the electrical couple, when folded is adhered to the second surface of the substrate so as to maintain the electrical couple in position.

20. A device according to claim 1, wherein the control means further comprises a circular housing, and wherein one of the electrical contacts on the housing defines a peripheral region and another of the contacts defines a central region, the contacts being separated by an annular region.

21. A device according to claim 1, wherein the control means comprises an electronic control unit having at least one lead extending therefrom to a contact for attachment to the delivery means.

* * * * *